(12) United States Patent
Grummt et al.

(10) Patent No.: US 7,157,246 B2
(45) Date of Patent: Jan. 2, 2007

(54) RNA POLYMERASE I TRANSCRIPTION FACTOR TIF-IA

(75) Inventors: Ingrid Grummt, Heidelberg (DE); Martin Vingron, Berlin (DE)

(73) Assignee: Deutsches Krebsforschungszentrum Stiftung des Oeffentlichen Rechts, Heidelberg (DE)

( * ) Notice: Subject to any disclaimer, the term of this patent is extended or adjusted under 35 U.S.C. 154(b) by 0 days.

(21) Appl. No.: 09/952,013

(22) Filed: Sep. 14, 2001

(65) Prior Publication Data

US 2002/0146801 A1    Oct. 10, 2002

Related U.S. Application Data

(63) Continuation of application No. PCT/DE00/00767, filed on Mar. 8, 2000.

(30) Foreign Application Priority Data

Mar. 17, 1999    (DE) ................ 199 11 992

(51) Int. Cl.
*C12P 21/06*    (2006.01)
*C07H 21/04*    (2006.01)

(52) U.S. Cl. ................ 435/69.1; 536/23.1

(58) Field of Classification Search ............. 435/325, 435/320.1, 419, 243, 69.1; 536/23.1, 23.5
See application file for complete search history.

(56) References Cited

FOREIGN PATENT DOCUMENTS

WO    WO 99/06549    *    2/1999    ............. 435/346

OTHER PUBLICATIONS

Sequence alignment of SEQ ID No:242 from WO 99/06549 with SEQ ID No: 1 of the instant application.*

Andreas Schnapp et al., "Function of the Growth-Regulated Transcription Initiation Factor TIF-IA in Iniation Complex Formation at the Murine Ribosomal Gene Promoter", Molecular and Cellular Biology, Nov. 1993, pp. 6723-6732, vol. 13, No. 11, American Society for Microbiology.

National Cancer Institute, cancer genome anatomy project (CGAP), "Genbank" accession No. AA213789, Feb. 1997.

Beth Moorefield et al., "RNA Polymerase I Transcription Factor Rrn3 is Functionally Conserved Between Yeast and Human", Proc. Natl. Acad. Sci., Apr. 25, 2000, pp. 4724-4729, vol. 97, No. 9.

Detlev Buttgereit et al., "Growth-Dependent Regulation of rRNA Synthesis is Mediated by a Transcription Initiation Factor (TIF-IA)", Nucleic Acids Research, 1985, pp. 8165-8179, vol. 13, No. 22, IRL Press Limited, Oxford, England.

Robert T. Yamamoto et al., "RRN3 Gene of *Saccharomyces cerevisiae* Encodes an Essential RNA Polymerase I Transcription Factor Which Interacts With The Polymerase Independently of DNA Template", The EMBO Journal, 1996, pp. 3964-3973, vol. 15, No. 15, Oxford University Press.

* cited by examiner

*Primary Examiner*—Celine Qian
*Assistant Examiner*—Tara L. Garvey
(74) *Attorney, Agent, or Firm*—Heller Ehrman LLP

(57) ABSTRACT

The present invention relates to an RNA polymerase I transcription factor TIF-IA and proteins related thereto, whose concentration and/or activity are correlated with the cell proliferation rate, and to DNA sequences encoding these proteins. The present invention also concerns ligands binding to an RNA polymerase I transcription factor TIF-IA and proteins related thereto, respectively, antagonists as well as antisense RNAs and/or ribozymes, directed against the TIF-IA expression. These compounds are of use for the prevention or treatment of diseases associated with an increased or reduced cell proliferation.

7 Claims, 6 Drawing Sheets

FIG. 1a

```
mmafentskrppqdfvapidqkkrkvqfsdstglvtlqpeeikdevfsaa----------            rrn3p
---------mpsiisstnpqyinkcvnngtmasstnvpdrtvgsksfassvskndgrlmq            pombe
--------------------mkrstanapklspkhesesdpkkvkleeeakptvnqa               cec36e8
-----------------------------mgavelmsdpsslctvenyvdnvd                   ATAC -mysrfvksalddldkndstqigiianqvalpskNP----eriNDKNLNILLDILSSNIN            rrn3p
qmlrafvnkald--dkaegnfagyedlrrqfaakSD--tkdapSSLQLQNLLSALTCNVS            pombe
ptgreivenylkgdvtaavlyrkicnaletfeqwES----eapKIQLLDQFLNIADAMEA            cec36e8
lsdtqlvqtvrkaltsvktgdsdlysemvgvmarDIkefkdpdVVAQLETVLKALSGAVA            ATAC RIESsrgtFLIQSIINFekWWE-LPPHTLSKYIYFIkilcssipkwwqdvsmilvscfil            rrn3p
RLDSsnss-LVMSVLDS--VWVsRDESFVRCYTRFLgnlisaqsnylplvmtmliqhml-            pombe
RTET-----LVKRLLSL--RWDkIPGSVIERFRNFLcelairhlcfteevysavverlvp            cec36e8
CIDVlhhqkLLSALFRMk-LWD-HRPDVMDALVNLVislavtsgkyldsclnmlvsnfvp            ATAC pi-----------KQTVch-------HDMLKYFLRMIPSSMGFIDTYLAKFFPNKNDTR             rrn3p
---------yrpdSLAI-----hyehaHMALKYVLELVPRAHSFLYSSILEEFPYKDESL            pombe
qisvteetgvvtlILTEkvqnehfemaHHIISSVLRCFPLSARALLKCVKRVMPHFTRPS            cec36e8
ppwvvnnls-hsrILNKki--dvlsrvHAALLKISILVPLTPSRLVPMLFQQMPKMHKKD            ATAC RKLVNYTSNLLKLRGYCSE--LGFQIWSLLIEKIISIDVELqneldelddddvddddleev          rrn3p
LAQMTYISNVLSICEYVPS--IKGPVLHAIIDKIIQIDVEIqvevdddde----------           pombe
VTVAGYMRNLILMQKYIPAs-ISKDVWEAVFERLAKDDTHN----------------w             cec36e8
HSIVIYVESLLKLENSSIGqvGGSMILGMVMERLRDLDVSRqnmliqlrs-------lei           ATAC dledddlddSgddddencgnsneeLrSgaadgsqsdsedm----------------                rrn3p
--eedevvtddDgtsnadsevitastLyE---------------------------                pombe
kceqneemsksP-----rlfalndiLiEevvegntndsedvtpeqleqrkgeqmiqyld             cec36e8
ewddipqddssRgmfdme--------L-Edaaegtmndgdclpvgplkq----------             ATAC ----diiegmdgteeynvELTQGiKELSTKLDSILtLVSTHVEEqvtpeslesgegvGVF            rrn3p
rhtaissemtsstiltppSLTDT-RQLMQQLDQLLyTLFSYLDSnlkstsrdr---yLVY            pombe
svctdvitfirssvdseiDEENG-NERTKLNDKWL-RNFKITGDkvlpke-------KLF            cec36e8
------------------DTSDG-SIVSKLLDKLMvVAFEHLEScqndgrld-----QVF            ATAC
```

FIG. 1b

```
NTLTTLFKTHVLPTYYTRSIQYIMFHVSQQQLEL-MDSFLVTLIDIsfavneaaekkiks    rrn3p
NSLIKSFVNTVLKTFRCRYTQFLIFWASQLDPEF-TDIFLGVLTEVcl---dpsqpytlr    pombe
DTFLECLESTMLNATHVQYVSFIWLYFCSLSQEY-EKKMLEHLWQVtirmprapadarks    cec36e8
ESLFKSFENFILNTYKSKFTQFLIFYACSLDPENcGVKFASKLVEI--------------   ATAC ---lqylgsyiarakklsrtqiifvasyltswlnRYVIEREEEVDQ-rggmERFKHFYAA    rrn3p
lsgamyigsyvarakalekntiqiivnmmtrwveAYLDQCENELSDdl--lSKHSVFYAI    pombe
qgaasylaaflarakyvkkstaftwleevyiwlrHYVDQFGSGSSQilpglQRHGTFYSV    cec36e8
---------flssnkhvatrqaslrlidecv---GYCRTCNDDTRP-----EAHQIFFSG   ATAC FQALCYIFCFRHNIFRDTDGN----------weceldkFFQRMVISKFNPLKFCNENVMLM   rrn3p
NQSIFYIFCFRWRELCVSDESesmeprpnewipgle-ILHRSVLSRLNPLRYCSPNIVLQ   pombe
SQAFFLVFAFRYKEFVKNKDMletirr---------wGVGRVVHSPELPLKYVSKPVARC   cec36e8
CQAIMYVLCFRMRSILDVPRFrsqlt-----------PLESILMHKLNPLMVCLPSVVAE  ATAC FARIAQQESVAYCFSiiennnneRLRGIIGKadsdkkensaqanttsssslatrqqfid   rrn3p
FAKVANHLNFMYVYSii----eqNRKGIFRE-----------------------gfdt    pombe
FSAITRSLQLVYCNHii------PIEEVQRP-------------------------     cec36e8
FLRQAKEGGLFIVSDsf-ifdddlLESELSRAfgg--------------------fer   ATAC LQSYFPYDPLFLKNYKILMKEYY--------------IEWSEASGEYESDGSDD----    rrn3p
MDAYFPFDPYRLTKSSIIVQPFY--------------NEWQQIPGLDDDEEEEDtdye   pombe
FDDMFPFDCYHLKESSKFMTPLMrkfsplaedmstltkaLCWNAATADKSEKSAEAvsss  cec36e8
LDTFFPFDPCLLKSSNSFISPNF--------------IYWSMVKATYDEDDDDNdaev   ATAC -------------------------------------------------------     rrn3p
sstvmlges-----------------------------------------pf----    pombe
egldfldeddammmggssgyrertfscgqs---------slinysatpglqtfnv----  cec36e8
ivngdedsdeddeadldyalnkmsitpkhsfknkmerdrllrmpsrirpstspesl---- ATAC
```

FIG. 2a

```
  1 GGAGCGGCCGCCCAGGTGCGGTCGCGTTAGTTCGGCCCAATGGCGGCACCGCTGCTTCAC
                                                 M  A  A  P  L  L  H  -

61 ACGCGTTTGCCGGGAGATGCGGCCGCTTCGTCCTCTGCAGTTAAGAAGCTGGGCGCGTCG
     T  R  L  P  G  D  A  A  A  S  S  S  A  V  K  K  L  G  A  S  -

120 AGGACTGGGATTTCAAATATGCGTGCATTAGAGAATGACTTTTTCAATTCTCCCCCAAGA
     R  T  G  I  S  N  M  R  A  L  E  N  D  F  F  N  S  P  P  R  -

181 AAAACTGTTCGGTTTGGTGGAACTGTGACAGAAGTCTTGCTGAAGTACAAAAAGGGTGAA
     K  T  V  R  F  G  G  T  V  T  E  V  L  L  K  Y  K  K  G  E  -

241 ACAAATGACTTTGAGTTGTTGAAGAACCAGCTGTTAGATCCAGACATAAAGGATGACCAG
     T  N  D  F  E  L  L  K  N  Q  L  L  D  P  D  I  K  D  D  P  -

301 ATCATCAACTGGCTGCTAGAATTCCGTTCTTCTATCATGTACTTGACAAAAGACTTTGAG
     I  I  N  W  L  L  E  F  R  S  S  I  M  Y  L  T  K  D  F  E  -

361 CAACTTATCAGTATTATATTAAGATTGCCTTGGTTGAATAGAAGTCAAACAGTAGTGGAA
     Q  L  I  S  I  I  L  R  L  P  W  L  N  R  S  Q  T  V  V  E  -

421 GAGTATTTGGCTTTTCTTGGTAATCTTGTATCAGCACAGACTGTTTTCCTCAGACCGTGT
     E  Y  L  A  F  L  G  N  L  V  S  A  Q  T  V  F  L  R  P  C  -

481 CTCAGCATGATTGCTTCCCATTTTGTGCCTCCCCGAGTGATCATTAAGGAAGGCGATGTA
     L  S  M  I  A  S  H  F  V  P  P  R  V  I  I  K  E  G  D  V  -

541 GATGTTTCAGATTCTGATGATGAAGATGATAATCTTCCTGCAAATTTTGACACATGTCAC
     D  V  S  D  S  D  D  E  D  D  N  L  P  A  N  F  D  T  C  H  -

601 AGAGCCTTGCAAATWATAGCAAGATATGTACCATCGACACCGTGGTTTCTCATGCCAATA
     R  A  L  Q  I  I  A  R  Y  V  P  S  T  P  W  F  L  M  P  I  -
```

FIG. 2b

```
 661 CTGGTGGAAAAATTTCCATTTGTTCGAAAATCAGAGAGAACACTGGAATGTTACGTTCAT
      L  V  E  K  F  P  F  V  R  K  S  E  R  T  L  E  C  Y  V  H  -

721 RACTTACTAAGGATTAGTGTATATTTTCCAACCTTGAGGCATGAAATTCTGGAGCTTATT
      ?  L  L  R  I  S  V  Y  F  P  T  L  R  H  E  I  L  E  L  I  -

781 ATTGAAAAACTACTCAAGTTGGATGTGAATGCATCCCGGCAGGGTATTGAAGATGCTGAA
      I  E  K  L  L  K  L  D  V  N  A  S  R  Q  G  I  E  D  A  E  -

841 GAAACAGCAACTCAAACTTGTGGTGGGACAGATTCCACGGAAGGATTGTTTAATATGGAT
      E  T  A  T  Q  T  C  G  G  T  D  S  T  E  G  L  F  N  M  D  -

901 GAAGATGAAGAAACTGAACATGAAACAAAGGCTGGTCCTGAACGGCTCGACCAGATGGTG
      E  D  E  E  T  E  H  E  T  K  A  G  P  E  R  L  D  Q  M  V  -

961 CATCCTGTAGCCGAGCGCCTGGACATCCTGATGTCTTTGGTTTTGTCCTACATGAAGGAT
      H  P  V  A  E  R  L  D  I  L  M  S  L  V  L  S  Y  M  K  D  -

1021 GTCTGCTATGTAGATGGTAAGGTTGATAACGGCAAAACAAAGGATCTATATCGCGACCTG
      V  C  Y  V  D  G  K  V  D  N  G  K  T  K  D  L  Y  R  D  L  -

1081 ATAAACATCTTTGACAAACTCCTGTTGCCCACCCATGCCTCCTGCCATGTACAGTTTTTC
      I  N  I  F  D  K  L  L  L  P  T  H  A  S  C  H  V  Q  F  F  -

1141 ATGTTTTACCTCTGTAGTTTCAAATTGGGATTCGCAGAGGCATTTTTGGAACATCTCTGG
      M  F  Y  L  C  S  F  K  L  G  F  A  E  A  F  L  E  H  L  W  -

1201 AAAAAATTGCAGGACCCAAGTAATCCTGCCATCATCAGGCAGGCTGCTGGAAATTATATT
      K  K  L  Q  D  P  S  N  P  A  I  I  R  Q  A  A  G  N  Y  I  -

1261 GGAAGCTTTTTGGCAAGAGCTAAATTTATTCCTCTTATTACTGTAAAATCATGCCTAGAT
      G  S  E  I  A  R  A  K  E  I  D  I  I  T  H  K  C  C  I  P
```

FIG. 2c

```
1321 CTTTTGGTTAACTGGCTGCACATATACCTTAATAACCAGGATTCGGGAACAAAGGCATTC
      L  L  V  N  W  L  H  I  Y  L  N  N  Q  D  S  G  T  K  A  F  -

1381 TGCGATGTTGCTCTCCATGGACCATTTTACTCAGCCTGCCAAGCTGTGTTCTACRCCTTT
      C  D  V  A  L  H  G  P  F  Y  S  A  C  Q  A  V  F  Y  ?  F  -

1441 GTTTTTAGACACAAGCAGCTTTTGAGCGGAAACCTGAAAGAAGGTTTGCAGTATCTTCAG
      V  F  R  H  K  Q  L  L  S  G  N  L  K  E  G  L  Q  Y  L  Q  -

1501 AGTCTGAATTTTGAGCGGATAGTGATGAGCCAGCTAAATCCCCTGAAGATTTGCCTGCCC
      S  L  N  F  E  R  I  V  M  S  Q  L  N  P  L  K  I  C  L  P  -

1561 TCAGTGGTTAACTTTTTTGCTGCAATCACAAATAAGTACCAGCTCGTCTTCTGCTACACC
      S  V  V  N  F  F  A  A  I  T  N  K  Y  Q  L  V  F  C  Y  T  -

1621 ATCATTGAGAGGAACAATCGCCAGATGCTGCCAGTCATTAGGAGTACCGCTGGAGGAGAC
      I  I  E  R  N  N  R  Q  M  L  P  V  I  R  S  T  A  G  G  D  -

1681 TCAGTGCAGATCTGCACAAACCCGCTGGACACCTTCTTCCCCTTTGATCCCTGTGTGCTG
      S  V  Q  I  C  T  N  P  L  D  T  F  F  P  F  D  P  C  V  L  -

1741 AAGAGGTCAAAGAAATTCATTGATCCTATTTATCAGGTGTGGGAAGACATGAGTGCTGAA
      K  R  S  K  K  F  I  D  P  I  Y  Q  V  W  E  D  M  S  A  E  -

1801 GAGCTACAGGAGTTCAAGAAACCCATGAAAAAGGACATAGTGGAAGATGAAGATGATGAC
      E  L  Q  E  F  K  K  P  M  K  K  D  I  V  E  D  E  D  D  D  -

1861 TTTCTGAAAGGCGAAGTGCCCCAGAATGATACCGTGATTGGGATCACACCAAGCTCCTTT
      F  L  K  G  E  V  P  Q  N  D  T  V  I  G  I  T  P  S  S  F  -

1921 GACACGCATTTCCGAAGTCCTTCAAGTAGTGTGGGCTCCCCACCCGTGTTGTACATGCAA
      D  T  H  F  R  S  P  S  S  S  V  G  S  P  P  V  L  Y  M  Q  -

1981 CCCAGTCCCCTCTGACGGCAGAAATTTGTGACTGAGATGTGACATTTGGGATTCCCCATC
      P  S  P  L  *
```

Lane 1: heart
Lane 2: brain
Lane 3: placenta
Lane 4: lungs
Lane 5: liver
Lane 6: sceletal muscle
Lane 7: kidney
Lane 8: pancreas

RNA POLYMERASE I TRANSCRIPTION FACTOR TIF-IA

This application is a continuation of PCT/DE00/00767, filed on Mar. 8, 2000. This application claims foreign priority to German patent application 19911992.9, filed on Mar. 17, 1999.

The present invention relates to an RNA polymerase I transcription factor TIF-IA and proteins related thereto, whose concentration and/or activity are correlated with the cell proliferation rate, as well as DNA sequences encoding these proteins. The present invention also concerns ligands binding to RNA polymerase I transcription factor TIF-IA and proteins related thereto, respectively, e.g. antibodies, antagonists, as well as antisense RNAs directed against the TIF-IA expression and ribozymes, respectively. Finally, the present invention relates to pharmaceutical preparations and diagnostic methods where the above compounds are used.

The synthesis of ribosomal RNAs (rRNAs) by RNA polymerase I (Pol I) is regulated with utmost efficiency as a function of external signals, such as growth factors, hormones, nutrients and effectors for growth and differentiation. Correspondingly, the rRNA synthesis rate is drastically increased in tumor cells which show uncontrolled cell growth (Grummt, I.: "Regulation of Mammalian Ribosomal Gene Transcription by RNA Polymerase I.", Progr. NAR & Mol. Biol. (1999) 62, 109–154). However, the molecular mechanisms which link the transcription activity of class I genes to cell growth are still widely unknown. Therefore, the elucidation of the processes by which extracellular signals are transmitted into the cell nucleus and nucleolus, respectively, where they influence the transcription rate positively or negatively, calls for the structural and functional analysis of the protein factors involved in the transcription process, the investigation of their interactions, and the identification of modifying enzymes, e.g. protein kinases and protein phosphatases which regulate the activity of certain transcription factors as a function of the cellular proliferation rate.

A factor which is responsible for the growth-dependent regulation of the rDNA transcription is TIF-IA whose concentration and/or activity fluctuates as a function of the proliferation rate of the cells. TIF-IA had been identified functionally in 1983 already (Buttgereit et al., Nucleic Acids Res. 13 (1985), 8165–8180) and characterized biochemically in the following years (Mahajan and Thompson, J. Biol. Chem. 265 (1990), 16225–16233; Schnapp et al., Mol. Cell. Biol. 13 (1993), 6723–6732). These investigations supplied the following important findings: (1) TIF-IA is an essential initiation factor for Pol I which seems to be functionally homologous to the bacterial σ-factor. As shown for the σ-factor, TIF-IA is also associated with the initiation-competent form of Pol I, the Pol I "holo enzyme", and is released by Pol I after the initiation reaction; (2) the amount and/or activity of TIF-IA correlates with the proliferation rate of the cells, i.e. extracts from growth-arrested cells are transcriptionally inactive, but they can be complemented by the addition of partially purified TIF-IA; and (3) the biochemical purification of TIF-IA resulted in the fact that less than one thousand TIF-IA molecules per se are present in exponentially growing cells.

Because of the biological properties of TIF-IA, it can be assumed that the latter can be useful for the prevention and/or treatment of diseases, where a stimulation of the cell proliferation by an activation of the cellular rRNA synthesis is therapeutically useful, e.g. to support the tissue regeneration after injuries or radiation therapy. On the other hand, it is also possible to use the inactivation of TIF-IA for the proliferation inhibition and/or for the prevention and/or treatment of diseases which are accompanied by an increased cell proliferation, e.g. tumoral diseases. Such an inactivation can take place on various levels, e.g. on a genetic level ("knock out", inhibition of the translation by antisense RNAs or ribozymes) or protein level (TIF-IA-inhibiting ligands or antagonists, kinase/phosphatase inhibitors, inhibition of the TIF-IA bonding to Pol I, etc.). However, a precondition for the above discussed therapeutic possibilities is the fact that TIF-IA and the TIF-IA-encoding gene, respectively, is available as a protein in sufficient amounts and in the purest possible form, which enables, on the one hand, the recombinant production thereof and, on the other hand, a treatment based on a gene therapy. However, even the partial purification of TIF-IA was formerly extremely difficult, since—as mentioned already—the protein is only present in very minor amounts in the cell and moreover is presumably very unstable. Although on the basis of several hundred liters of cultured cells, TIF-IA could be purified by a combination of nine chromatographic steps, the TIF-IA activity correlating with a 75 kDa protein (Schnapp et al., supra), neither the purity nor the amount of biochemically purified TIF-IA have been sufficient so far to be able to use it therapeutically and determine partial amino acid sequences, respectively, which would permit the development of probes for the TIF-IA-encoding gene.

Thus, the subject matter of the present invention relates to a DNA sequence which codes for an RNA polymerase I transcription factor TIF-IA with the amino acid sequence shown in FIGS. 2a–2c, the DNA sequence containing the nucleic acid sequence shown in FIGS. 2a–2c in a preferred embodiment.

The solution to this technical problem is obtained by the provision of the embodiments characterized in the claims.

Thus, the subject matter of the present invention relates to a DNA sequence which codes for an RNA polymerase I transcription factor TIF-IA with the amino acid sequence shown in FIG. 2, the DNA sequence containing the nucleic acid sequence shown in FIG. 2 in a preferred embodiment.

The present invention is based on the isolation of a cDNA sequence which codes for human TIF-IA. Since it was formerly not possible to provide TIF-IA in amounts and in a purity such that—based on a partial amino acid sequence, for example—probes for a successful cloning of the gene could be developed, the present invention used another strategy for determining the TIF-IA-encoding gene. In this connection, gene libraries were screened for DNA sequences having homologies to genes responsible for the Pol I transcription in yeast. This procedure which finally resulted in the isolation of the TIF-IA-encoding clone, is described in detail in the below examples.

The present invention also relates to a DNA sequence which codes for a protein having the biological properties of an RNA polymerase I transcription factor TIF-IA and because of the degeneration of the genetic code differs from the DNA sequence of FIGS. 2a–2c in the codon sequence which sequence hybridizes with the above DNA sequences or which is a fragment, an allelic variant or another variant of the above DNA sequences.

The expression "hybridize" used in the present invention refers to conventional hybridization conditions, preferably to hybridization conditions where 5×SSPE, 1% SDS, 1×Denhardt solution are used as solution and/or the hybridization temperatures are between 35° C. and 70° C., preferably 65° C. After the hybridization, washing is first carried out with 2×SSC, 1% SDS and then with 0.2×SSC at temperatures between 35° C. and 70° C., preferably at 65° C.

(regarding the definition of SSPE, SSC and Denhardt solution see Sambrook et al., Molecular Cloning: A Laboratory Manual, 2nd edition, Cold Spring Harbor Laboratory Press, Cold Spring Harbor N.Y. (1989)). Stringent hybridization conditions, as described in Sambrook et al., supra, for example, are particularly preferred.

The expressions "variants" or "fragment" used in the present invention comprise DNA sequences which differ from the sequences indicated in FIGS. 2a–2c by deletion(s), insertion(s), exchange(s) and/or other modifications known in the art and comprise a fragment of the original nucleic acid molecule, respectively, the protein encoded by these DNA sequences still having the biological properties of TIF-IA and being biologically active in mammals. This also includes allel variants.

Methods of producing the above modifications in the nucleic acid sequence are known to a person skilled in the art and described in standard works of molecular biology, e.g. in Sambrook et al, supra. The person skilled in the art can also determine whether a protein encoded by a nucleic acid sequence modified in such a way still has the biological properties of TIF-IA.

The synthesis of TIF-IA and related proteins, respectively, can be reduced or eliminated by lowering or inhibiting the expression of the above described DNA sequences, which is desirable e.g. for the conditions described in the introductory part. Therefore, another preferred embodiment of the present invention relates to an antisense RNA which is characterized in that it is complementary to the above DNA sequences and can reduce or inhibit the synthesis of the TIF-IA encoded by these DNA sequences and to a ribozyme which is characterized in that it is complementary to the above DNA sequences and can bind specifically to the RNA transcribed by these DNA sequences and cleave them, so that the synthesis of the TIF-IA encoded by these DNA sequences is also reduced or inhibited. These antisense RNAs and ribozymes are preferably complementary to an encoding region of the mRNA. Based on the disclosed DNA sequences, the person skilled in the art can produce and use suitable antisense RNAs. Suitable procedures are described in EB-B1 0 223 399 or EP-A1 0 458, for example. Ribozymes are RNA enzymes and consist of a single RNA strand. They can cleave intermolecularly other RNAs, e.g. the mRNAs transcribed by the DNA sequences according to the invention. In principle, these ribozymes must have two domains, (1) a catalytic domain and (2) a domain which is complementary to the target RNA and can bind thereto, which is the precondition for a cleavage of the target RNA. Based on procedures described in the literature, it is meanwhile possible to construct specific ribozymes which excise a desired RNA at a certain preselected site (see e.g. Tanner et al., in: Antisense Research and Applications, CRC Press, Inc. (1993), 415–426). The antisense-RNAs and/or ribozymes according to the invention preferably have a region which is complementary to the target DNA over a length of 12 nucleotides, preferably 15 nucleotides, more preferably 20 nucleotides.

The DNA sequences according to the invention and the DNAs encoding the above described antisense RNAs or ribozymes, respectively, can also be inserted in a vector and expression vector, respectively. Thus, the present invention also comprises vectors containing these DNA sequences and such expression vectors, respectively. The term "vector" refers to a plasmid (pUC18, pBR322, pBlueScript, etc.), to a virus or another suitable vehicle. In a preferred embodiment, the DNA molecule according to the invention is functionally linked in the vector to regulatory elements which permit the expression thereof in prokaryotic or eukaryotic host cells. In addition to the regulatory elements, e.g. a promoter, such vectors typically contain a replication origin and specific genes which permit the phenotypic selection of a transformed host cell. The regulatory elements are the lac-, trp-promoter or T7 promoter for the expression in prokaryotes, e.g. E. coli, and the AOX1 or GAL1 promoter for the expression in eukaryotes, in yeast, and the CMV, SV40, RVS-40 promoter, CMV or SV40 enhancer for the expression in animal cells. Further examples of suitable promoters are the metallothionein I and the polyhedrin promoters. Suitable expression vectors for E. coli are e.g. PGEMEX, pUC derivatives, pGEX-2T, pET3b and pQE-8, the latter being preferred. The vectors suitable for the expression in yeast include pV100 and Ycpad1, and those for the expression in mammal cells comprise pMSXND, pKCR, pEFBOS, cDM8 and pCEV4. Vectors for the expression in insect cells, which are derived from baculovirus, e.g. pAcSGHisNT-A, are also counted among the expression vectors according to the invention.

General methods known in the art can be used for the construction of expression vectors which contain the DNA sequences according to the invention and suitable control sequences. These methods include e.g. in vitro recombination techniques, synthetic methods, as well as in vivo recombination methods as described in Sambrook et al., supra, for example. The DNA sequences according to the invention can also be inserted in combination with a DNA coding for another protein and peptide, respectively, so that the DNA sequences according to the invention can be expressed in the form of a fusion protein, for example.

The present invention also concerns host cells containing the above described vectors. These host cells include bacteria (e.g. the E. coli strains HB101, DH1, x1776, JM101, JM109, BL21 and SG13009), yeast, preferably S. cerevisiae, insect cells, preferably sf9 cells, and animal cells, preferably mammalian cells. Preferred mammalian cells are CHO-VERO, BHK, HeLa, COS, MDCK, 293 and WI38 cells. Methods of transforming these host cells, of phenotypically selecting transformants and of expressing the DNA molecules according to the invention by using the above described vectors are known in the art.

The present invention also relates to an RNA polymerase I transcription factor TIF-IA which is encoded by the DNA sequences according to the invention and proteins having the biological activity thereof, respectively, as well as to methods for the recombinant production thereof by using the expression vectors according to the invention. The method according to the invention comprises the culturing of the above described host cells under conditions which permit the expression of the protein (and fusion protein, respectively) (preferably stable expression) and the collection of the protein from the culture or the host cells. The person skilled in the art knows conditions of culturing transformed host cells and transfected host cells, respectively. Suitable purification methods (e.g. preparative chromatography, affinity chromatography, e.g. immunoaffinity chromatography, HPLC, etc.) are also generally known.

A preferred embodiment of the present invention relates to ligands against the above described proteins according to the invention (TIF-IA or related proteins). These ligands can be used e.g. in diagnostic assays or for therapeutic purposes, the attachment to the target molecule, i.-e. TIF-IA, being followed by the inhibition thereof, i.e. it can no longer bond to its target, Pol I, and no longer activate them. The person skilled in the art is familiar with methods of isolating and synthesizing, respectively, such ligands. For example, possibly useful activity-inhibiting compounds can be screened in extracts of natural products as starting material. Such extracts can originate from mushrooms, actinomycetes, algae, insects, protozoa, plants and bacteria, for example.

The ligand according to the invention is preferably an antibody or a fragment thereof. These antibodies can be monoclonal, polyclonal or synthetic antibodies or fragments thereof. In this connection, the expression "fragment" refers to all parts of the monoclonal antibody (e.g. Fab, Fv or single chain Fv fragments) which have the same epitope specificity as the complete antibody. The person skilled in the art is familiar with the production of such fragments. The antibodies according to the invention are preferably monoclonal antibodies. The antibodies according to the invention can be produced according to standard methods, preferably the TIF-IA encoded by the DNA sequences according to the invention or a synthetic fragment thereof serving as an immunogen. The person skilled in the art knows methods of obtaining monoclonal antibodies.

In a particularly preferred embodiment said monoclonal antibody is an antibody originating from an animal (e.g. mouse), a humanized antibody or a chimeric antibody or a fragment thereof. Chimeric antibodies, antibodies similar to human antibodies or humanized antibodies have a reduced potential antigenicity, but their affinity over the target is not reduced. The production of chimeric and humanized antibodies and of antibodies similar to human antibodies, respectively, has been described in detail (see e.g. Queen et al., Proc. Natl. Acad. Sci. USA 86 (1989), 10029, and Verhoeyan et al., Science 239 (1988), 1534). Humanized immunoglobulins have variable framework regions which originate substantially from a human immunoglobulin (with the designation acceptor immunoglobulin) and the complementarity of the determining regions which originate substantially from a non-human immunoglobulin (e.g. from a mouse) (with the designation of donor immunoglobulin). The constant region(s) originate(s), if present, also substantially from a human immunoglobulin. When administered to human patients, humanized (as well as human) antibodies offer a number of advantages over antibodies from mice or another species: (a) the human immune system should not regard the framework or the constant region of the humanized antibody as foreign and therefore the antibody response to such an injected antibody should be less than to a completely foreign mouse antibody or a partially foreign chimeric antibody; (b) since the effector region of the humanized antibody is human, it interacts better with other parts of the human immune system, and (c) injected humanized antibodies have a half life which is substantially equivalent to that of naturally occurring human antibodies, which permits the administration of doses smaller and less frequent as compared to antibodies of other species.

The antibodies according to the invention can also be used e.g. for the immunoprecipitation of the TIF-IA according to the invention, for the isolation of related proteins from cDNA expression libraries or for diagnostic purposes (see below). The present invention also relates to a hybridoma which produces the above described monoclonal antibody.

In a further preferred embodiment, the present invention relates to antagonists for TIF-IA and proteins related thereto, respectively. They permit in vivo also an inhibition of the rRNA transcription rate. The possible antagonists include peptides which can be obtained by screening e.g. oligopeptides with sequences produced according to the random principle so as to discover TIF-IA inhibitors. Such peptides can be used directly as active substances or to discover the sense or position of a functional group which can inhibit TIF-IA activity, which in turn results in the construction and testing of an inhibitory small molecule or wherein the peptide becomes the backbone of chemical modification which increases the possible pharmacological uses thereof. The peptide may be structural imitators, but it is also possible to use molecule modulating programs to construct imitators—based on the characteristic secondary and/or tertiary structure of TIF-IA. Such structural imitators can then be used in vivo as TIF-IA inhibitors. The compounds active as antagonists also include e.g. inactive TIF-IA molecules. If they are expressed and administered, respectively, in sufficiently high concentration, this will result in an exhaustion of necessary active TIF-IA molecules, so that they function as TIF-IA antagonists.

The present invention also permits the execution of therapeutic measures of the above discussed defects of cell proliferation and the diseases connected therewith, respectively, i.e. the above described DNA sequences, antisense RNAs, ribozymes, ligands and antagonists according to the invention can also be used for the production of a pharmaceutical preparation, e.g. for controlling the expression of the TIF-IA (or the protein related thereto) or for exchanging a mutated form of the gene by a functional form, e.g., on the one hand, for the production of a pharmaceutical preparation for the prevention or treatment of diseases which are associated with an increased cell proliferation or for inhibiting the cell proliferation, particularly tumoral diseases and, on the other hand, for the production of a pharmaceutical preparation for the prevention or treatment of diseases which are associated with the reduced cell proliferation or for stimulating cell proliferation, e.g. for promoting the tissue regeneration. For example, the TIF-IA according to the invention can be introduced into mammals, particularly human beings, by common measures. For this purpose, it may be favorable to link the protein to a protein which is not regarded as foreign by the particular body, e.g. transferrin or bovine serum albumin (BSA). An inventive DNA sequence, antisense RNA or ribozyme can also be introduced into, and expressed in, mammals, particularly human beings. By means of a ligand according to the invention, e.g. a monoclonal antibody, it is possible to control and regulate the expression of TIF-IA and the related proteins, respectively. Antagonists for TIF-IA can also be used to thus reduce, or even fully block, the effect of active TIF-IA.

Thus, the present invention also relates to a pharmaceutical preparation which contains the above described DNA sequences, antisense RNA, the ribozyme, the expression vector, the protein according to the invention, the ligand or antagonist. This pharmaceutical preparation optionally contains additionally a pharmaceutically compatible carrier. The person skilled in the art knows suitable carriers and the formulation of such pharmaceutical preparations. Suitable carriers are e.g. phosphate-buffered salt solutions, water, emulsions, e.g. oil-in-water emulsions, wetting agents, sterile solutions, etc. The pharmaceutical preparations can be administered orally or parenterally. The methods of parenteral administration include the topical, intraarterial, intramuscular, subcutaneous, intramedullary, intrathecal, intraventricular, intravenous, intraperitoneal or intranasal administration. The suitable dosage is determined by a physician and depends on various factors, e.g. on the patient's age, sex, weight, the stage of the disease, the kind of administration, etc.

The above described DNA sequences are preferably inserted in a vector suitable for gene therapy, e.g. under the control of a tissue-specific promoter, and introduced into the cells. In a preferred embodiment, the vector containing the above described DNA sequences is a virus, e.g. an adenovirus, vaccinia virus or adenovirus. Retroviruses are particularly preferred. Examples of suitable retroviruses are MoMuLV, HaMuSV, MuMTV, RSV or GaLV. For the purposes of gene therapy, the DNA sequences according to the invention can also be transported to the target cells in the form of colloidal dispersions. They include e.g. liposomes or lipoplexes (Mannino et al., Biotechniques 6 (1988), 682). This gene therapy can be used for both the increase in the proliferation rate of the cells (e.g. using a vector which contains the gene for active TIF-IA) and the reduction of the proliferation rate (using a vector which contains a gene for a ribozyme, an antisense RNA or an inactive form of TIF-IA ("knock out").

The present invention also enables the investigation of defects of TIF-IA expression and/or cell proliferation on a genetic level. By means of a DNA sequence according to the invention and/or probes or primers derived therefrom it is possible to determine in mammals, particularly human beings, whether they contain a modified TIF-IA gene which results in a mutated form of the protein which is no longer biologically active or whether e.g. the TIF-IA is expressed too slightly or too strongly. For this purpose, the person skilled in the art can carry out common methods, such as reverse transcription, PCR, LCR, hybridization and sequencing. The ligands according to the invention, e.g. the antibodies or fragments thereof, are also suitable for diagnosis, i.e. e.g. for the detection of the presence and/or the concentration of the TIF-IA, a shortened or extended form of this protein, etc., in a sample. The antibodies can be bonded e.g. in immunoassays in liquid phase or to a solid carrier. In this connection, the antibodies can be labeled in various ways. Suitable markers and marking methods are known in the art. Examples of immunoassays are ELISA and RIA.

Thus, the present invention also relates to a diagnostic method of detecting a defective TIF-IA expression, in which a sample is contacted with the DNA sequence according to the invention or the ligand according to the invention, e.g. a monoclonal antibody or a fragment thereof and then it is determined directly or indirectly whether the concentration, length and/or sequence of the RNA polymerase I transcription factor TIF-IA or the mRNA encoding it differ from a control sample. The probes usable for this diagnostic method also comprise primers based on the DNA sequences according to the invention, e.g. for a PCR.

Finally, the present invention relates to a diagnostic kit for carrying out the above described diagnostic method, which contains a DNA sequence according to the invention or the above described ligand according to the invention, e.g. a monoclonal antibody or the fragment thereof. Depending on the arrangement of the diagnostic kit, the DNA sequence and the ligand, respectively, can be immobilized.

BRIEF DESCRIPTION OF THE FIGURES

FIGS. 1a and 1b: Comparison of the amino acid sequences of rrn 3p from *S. cerevisiae* (rrn3p) (SEQ ID NO:3) and homologous proteins from *S. pombe* (pombe) (SEQ ID NO:4), *C. elegans* (cec37a8) (SEQ ID NO:5) and *Arabidopsis thaliana* (ATAC) (SEQ ID NO:6).

FIGS. 2a, 2b, and 2c: Human cDNA sequence TIF-IA and derived amino acid sequence (SEQ ID NOs 1 and 2, respectively).

Figure 3:
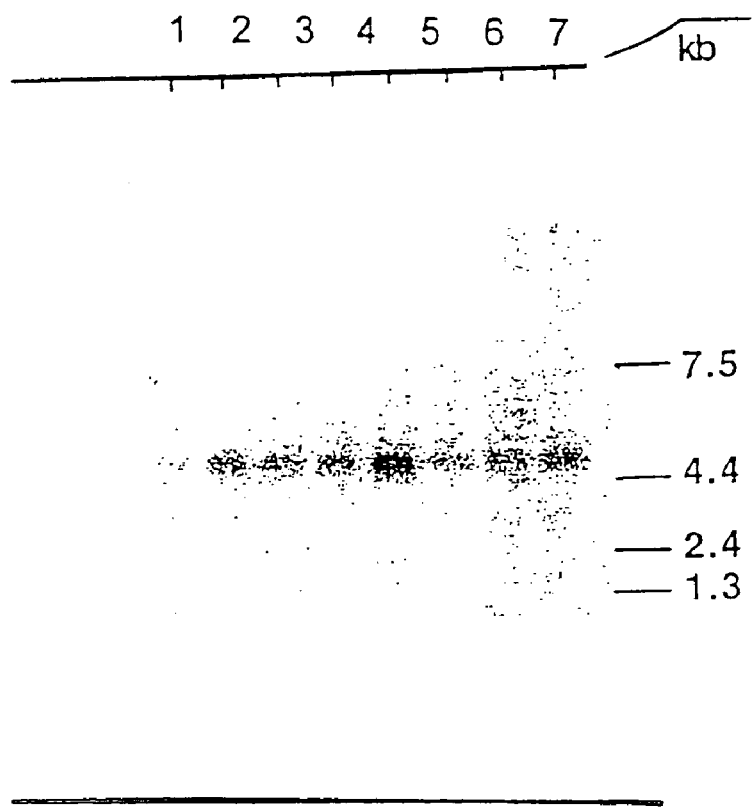
FIG. 3: Northern blot analysis

For the detection of TIF-IA sequences, RNAs extracted from various tissues (Clontech: 7760-1) were hybridized with radioactively labeled TIF-IA cDNA (Clon pBS-hTIF-IA) and then an radioautography was made.

The following examples explain the invention.

EXAMPLE 1

Identification of a TIF-IA cDNA Sequence

Gene products of yeast genes are known which are required for the Pol I transcription in *S. cerevisiae*. One of the gene products, rrn3p, is a 72 kDa protein which is associated with the third biggest subpart of Pol I (RPA49). It seems that it is either not present in stationary yeast cultures or transcriptionally inactive. Such properties are also characteristic of TIF-IA. Therefore, the applicant assumed that rrn3p and TIF-IA could be functionally homologous proteins. For this reason, he conducted an extensive search into various data banks to obtain information about the possible existence of an rrn3p-homologous protein in other organisms. By means of the "BLAST" program, he identified homologies between rrn3p from *S. cerevisiae* and a gene product from *Arabidopsis thaliana* (PID:g3132470) and a gene product from *S. pombe* (Swissprot ID YAQA_SCHPO), a gene product from *C. elegans* (PID:g3924707). The comparisons of the amino acid sequences are shown in FIGS. 1a–1b. They were carried out according to the algorithm from Vingron and Argos, J. Mol. Biol. 218 (1991), 33–43 and show the conserved regions in capital letters. The following consensus sequence for the C-terminal region could be derived therefrom (SEQ ID NO:7):

```
FNSLFKSFENTVLNTYKSRYTQFLIFYACSLDPENCDXFLSKLVEVFLSSNKAXAKRQ

ASARYIGSYVARAKTLNKDTIPXXXXXXXXXXXXXXXXXXXXXXXXXXXERHQIFYS

GCQAIFYVFCFRMREFLDVDRFRSQETRXXXERIVMSKLNPLKYCSPNVVLEFARIAK

ELGLFYVSSIIEFNDLLRS
```

By means of this core sequence, the applicant screened human ESTs and genomic sequence libraries. In this connection, three homologous regions were found in the genomic sequence of a "BAC" clone (CIT987SK-270G1, "Genbank" accession number AF001549). An exon prediction was calculated in a region of about 10,000 bases, which contains the homologies found, by means of the "GEN-SCAN" program. It confirmed the three discovered homologous regions in the conserved region as coding sequence. On the basis of this sequence, the 5' end of the gene homologous to rrn3p was determined by a 5'RACE from a human fetal cDNA library. By "gene walking", well-calculated PCR strategies, hybridization techniques, 3'RACE, sequencing and joining of the individual gene sections a cDNA clone was finally obtained which codes for TIF-JA with a molecular weight of about 75 kDa. The nucleic acid sequence and the amino acid sequence derived therefrom are shown in FIGS. 2a–2c. This cDNA clone was referred to as pBS-hTIF-IA. It was deposited with the DSMZ (Deutsche Sammlung von Mikroorganismen und Zellkulturen [German-type collection of microorganisms and cell cultures]under DSM 12707 on Feb. 25, 1999.

EXAMPLE 2

Detection of TIF-IA Sequences in Tissues

Purchasable filters (Clontech: 7760-1) which contain RNAs from heart, brain, placenta, lungs, liver, skeletal muscles, kidney and pancreas, were subjected to hybridization with [$\alpha^{32}$P] dCTP-labeled pBS-hTIF-IA cDNA of Example 1. The hybridization was made at 65° C. in 5×SSPE, 1% SDS, 1×Denhardt solution. Following hybridization, washing was carried out first with 2×SSC, 1% SDS and then with 0.2×SSC at 65° C.

It showed that TIF-IA sequences are expressed in strongly differing way in the most varying tissues.

EXAMPLE 3

Preparation and Purification of an RNA Polymerase I Transcription Factor TIF-IA According to the Invention The DNA of FIGS. 2a–2c was provided with BAMHI linkers, subsequently cleaved by BamHI and inserted in the expression vector pQE-8 (Qiagen company) cleaved by BamHI. The expression plasmid pQE-8/TIF-IA was obtained. Such a plasmid codes for a fusion protein from 6 histidine residues (N terminus partner) and the TIF-JA of FIGS. 2a–2c according to the invention (C terminus partner). pQE-8/TIF-IA was used for the transformation of *E. coli* SG 13009 (cf. Gottesman, S. et al., J. Bacteriol. 148, (1981), 265–273). The bacteria were cultured in an LB broth with 100 µg/ml ampicillin and 25 µg/ml kanamycin and induced with 60 µM isopropyl-β-D-thiogalactopyranoside (IPTG) for 4 hours. Lysis of the bacteria was achieved by the addition of 6 M guanidine hydrochloride. Then, a chromatography (Ni-NTA resin) was carried out with the lysate in the presence of 8 M urea in accordance with the instructions from the manufacturer (Qiagen) of the chromatography material. The bonded fusion protein was eluted in a buffer having a pH of 3.5. Following its neutralization, the fusion protein was subjected to an 18% SDS polyacrylamide gel electrophoresis and stained using coomassie blue (cf. Thomas, J. O. and Kornberg, R. D., J. Mol. Biol. 149 (1975), 709–733).

It showed that a (fusion) protein according to the invention can be produced in highly pure form.

The invention claimed is:

1. A substantially isolated nucleic acid, the sequence of which comprises a sequence selected from the group consisting of:
   (i) a sequence as set forth in SEQ ID NO:1, wherein the sequence encodes a polypeptide having TIF-IA activity; and
   (ii) a sequence that encodes SEQ ID NO:2.

2. An expression vector comprising a nucleic acid sequence according to claim 1.

3. An isolated host cell comprising an expression vector of claim 2.

4. A method of producing an RNA polymerase I transcription factor TIF-IA comprising recombinant expression of an isolated nucleic acid sequence of claim 1.

5. The method of claim 4, comprising culturing a host cell under suitable conditions, wherein said host cell comprises an expression vector comprising a nucleic acid sequence selected from the group consisting of:
   (i) a sequence as set forth in SEQ ID NO:1, wherein the sequence encodes an RNA polymerase I transcription factor TIF-IA; and
   (ii) a sequence that encodes SEQ ID NO:2.

6. A substantially isolated nucleic acid, the sequence of which comprises SEQ ID NO:1.

7. A substantially isolated nucleic acid sequence that encodes a polypeptide sequence as set forth in SEQ ID NO:2, wherein the polypeptide has TIF-IA activity.

* * * * *

SEQUENCE LISTING

```
<160> NUMBER OF SEQ ID NOS: 7

<210> SEQ ID NO 1
<211> LENGTH: 2040
<212> TYPE: DNA
<213> ORGANISM: Homo sapiens
<220> FEATURE:
<221> NAME/KEY: CDS
<222> LOCATION: (40)..(1992)
<223> OTHER INFORMATION:
<221> NAME/KEY: misc_feature
<222> LOCATION: (721)..(721)
<223> OTHER INFORMATION: n is a, c, g or t
<221> NAME/KEY: misc_feature
<222> LOCATION: (1435)..(1435)
<223> OTHER INFORMATION: n is a, c, g or t

<400> SEQUENCE: 1
ggagcggccg cccaggtgcg gtcgcgttag ttcggccca atg gcg gca ccg ctg         54
                                             Met Ala Ala Pro Leu
                                              1               5 ctt cac acg cgt ttg ccg gga gat gcg gcc gct tcg tcc tct gca gtt      102
Leu His Thr Arg Leu Pro Gly Asp Ala Ala Ala Ser Ser Ser Ala Val
             10                  15                  20 aag aag ctg ggc gcg tcg agg act ggg att tca aat atg cgt gca tta      150
Lys Lys Leu Gly Ala Ser Arg Thr Gly Ile Ser Asn Met Arg Ala Leu
                 25                  30                  35 gag aat gac ttt ttc aat tct ccc cca aga aaa act gtt cgg ttt ggt      198
Glu Asn Asp Phe Phe Asn Ser Pro Pro Arg Lys Thr Val Arg Phe Gly
             40                  45                  50 gga act gtg aca gaa gtc ttg ctg aag tac aaa aag ggt gaa aca aat      246
Gly Thr Val Thr Glu Val Leu Leu Lys Tyr Lys Lys Gly Glu Thr Asn
     55                  60                  65 gac ttt gag ttg ttg aag aac cag ctg tta gat cca gac ata aag gat      294
Asp Phe Glu Leu Leu Lys Asn Gln Leu Leu Asp Pro Asp Ile Lys Asp
 70                  75                  80                  85
```

-continued

| | |
|---|---|
| gac cag atc atc aac tgg ctg cta gaa ttc cgt tct tct atc atg tac<br>Asp Gln Ile Ile Asn Trp Leu Leu Glu Phe Arg Ser Ser Ile Met Tyr<br>                      90                          95                          100 | 342 |
| ttg aca aaa gac ttt gag caa ctt atc agt att ata tta aga ttg cct<br>Leu Thr Lys Asp Phe Glu Gln Leu Ile Ser Ile Ile Leu Arg Leu Pro<br>                 105                        110                        115 | 390 |
| tgg ttg aat aga agt caa aca gta gtg gaa gag tat ttg gct ttt ctt<br>Trp Leu Asn Arg Ser Gln Thr Val Val Glu Glu Tyr Leu Ala Phe Leu<br>        120                        125                        130 | 438 |
| ggt aat ctt gta tca gca cag act gtt ttc ctc aga ccg tgt ctc agc<br>Gly Asn Leu Val Ser Ala Gln Thr Val Phe Leu Arg Pro Cys Leu Ser<br>           135                        140                        145 | 486 |
| atg att gct tcc cat ttt gtg cct ccc cga gtg atc att aag gaa ggc<br>Met Ile Ala Ser His Phe Val Pro Pro Arg Val Ile Ile Lys Glu Gly<br>150                        155                        160                        165 | 534 |
| gat gta gat gtt tca gat tct gat gat gaa gat gat aat ctt cct gca<br>Asp Val Asp Val Ser Asp Ser Asp Asp Glu Asp Asp Asn Leu Pro Ala<br>                   170                        175                        180 | 582 |
| aat ttt gac aca tgt cac aga gcc ttg caa ata ata gca aga tat gta<br>Asn Phe Asp Thr Cys His Arg Ala Leu Gln Ile Ile Ala Arg Tyr Val<br>              185                        190                        195 | 630 |
| cca tcg aca ccg tgg ttt ctc atg cca ata ctg gtg gaa aaa ttt cca<br>Pro Ser Thr Pro Trp Phe Leu Met Pro Ile Leu Val Glu Lys Phe Pro<br>        200                        205                        210 | 678 |
| ttt gtt cga aaa tca gag aga aca ctg gaa tgt tac gtt cat nac tta<br>Phe Val Arg Lys Ser Glu Arg Thr Leu Glu Cys Tyr Val His Xaa Leu<br>           215                        220                        225 | 726 |
| cta agg att agt gta tat ttt cca acc ttg agg cat gaa att ctg gag<br>Leu Arg Ile Ser Val Tyr Phe Pro Thr Leu Arg His Glu Ile Leu Glu<br>230                        235                        240                        245 | 774 |
| ctt att att gaa aaa cta ctc aag ttg gat gtg aat gca tcc cgg cag<br>Leu Ile Ile Glu Lys Leu Leu Lys Leu Asp Val Asn Ala Ser Arg Gln<br>                 250                        255                        260 | 822 |
| ggt att gaa gat gct gaa gaa aca gca act caa act tgt ggt ggg aca<br>Gly Ile Glu Asp Ala Glu Glu Thr Ala Thr Gln Thr Cys Gly Gly Thr<br>              265                        270                        275 | 870 |
| gat tcc acg gaa gga ttg ttt aat atg gat gaa gat gaa gaa act gaa<br>Asp Ser Thr Glu Gly Leu Phe Asn Met Asp Glu Asp Glu Glu Thr Glu<br>        280                        285                        290 | 918 |
| cat gaa aca aag gct ggt cct gaa cgg ctc gac cag atg gtg cat cct<br>His Glu Thr Lys Ala Gly Pro Glu Arg Leu Asp Gln Met Val His Pro<br>           295                        300                        305 | 966 |
| gta gcc gag cgc ctg gac atc ctg atg tct ttg gtt ttg tcc tac atg<br>Val Ala Glu Arg Leu Asp Ile Leu Met Ser Leu Val Leu Ser Tyr Met<br>310                        315                        320                        325 | 1014 |
| aag gat gtc tgc tat gta gat ggt aag gtt gat aac ggc aaa aca aag<br>Lys Asp Val Cys Tyr Val Asp Gly Lys Val Asp Asn Gly Lys Thr Lys<br>                 330                        335                        340 | 1062 |
| gat cta tat cgc gac ctg ata aac atc ttt gac aaa ctc ctg ttg ccc<br>Asp Leu Tyr Arg Asp Leu Ile Asn Ile Phe Asp Lys Leu Leu Leu Pro<br>                 345                        350                        355 | 1110 |
| acc cat gcc tcc tgc cat gta cag ttt ttc atg ttt tac ctc tgt agt<br>Thr His Ala Ser Cys His Val Gln Phe Phe Met Phe Tyr Leu Cys Ser<br>        360                        365                        370 | 1158 |
| ttc aaa ttg gga ttc gca gag gca ttt gaa cat ctc tgg aaa aaa<br>Phe Lys Leu Gly Phe Ala Glu Ala Phe Leu Glu His Leu Trp Lys Lys<br>           375                        380                        385 | 1206 |
| ttg cag gac cca agt aat cct gcc atc atc agg cag gct gct gga aat<br>Leu Gln Asp Pro Ser Asn Pro Ala Ile Ile Arg Gln Ala Ala Gly Asn<br>390                        395                        400                        405 | 1254 |

-continued

```
tat att gga agc ttt ttg gca aga gct aaa ttt att cct ctt att act     1302
Tyr Ile Gly Ser Phe Leu Ala Arg Ala Lys Phe Ile Pro Leu Ile Thr
            410                 415                 420 gta aaa tca tgc cta gat ctt ttg gtt aac tgg ctg cac ata tac ctt     1350
Val Lys Ser Cys Leu Asp Leu Leu Val Asn Trp Leu His Ile Tyr Leu
            425                 430                 435 aat aac cag gat tcg gga aca aag gca ttc tgc gat gtt gct ctc cat     1398
Asn Asn Gln Asp Ser Gly Thr Lys Ala Phe Cys Asp Val Ala Leu His
            440                 445                 450 gga cca ttt tac tca gcc tgc caa gct gtg ttc tac ncc ttt gtt ttt     1446
Gly Pro Phe Tyr Ser Ala Cys Gln Ala Val Phe Tyr Xaa Phe Val Phe
    455                 460                 465 aga cac aag cag ctt ttg agc gga aac ctg aaa gaa ggt ttg cag tat     1494
Arg His Lys Gln Leu Leu Ser Gly Asn Leu Lys Glu Gly Leu Gln Tyr
470                 475                 480                 485 ctt cag agt ctg aat ttt gag cgg ata gtg atg agc cag cta aat ccc     1542
Leu Gln Ser Leu Asn Phe Glu Arg Ile Val Met Ser Gln Leu Asn Pro
                490                 495                 500 ctg aag att tgc ctg ccc tca gtg gtt aac ttt ttt gct gca atc aca     1590
Leu Lys Ile Cys Leu Pro Ser Val Val Asn Phe Phe Ala Ala Ile Thr
            505                 510                 515 aat aag tac cag ctc gtc ttc tgc tac acc atc att gag agg aac aat     1638
Asn Lys Tyr Gln Leu Val Phe Cys Tyr Thr Ile Ile Glu Arg Asn Asn
            520                 525                 530 cgc cag atg ctg cca gtc att agg agt acc gct gga gga gac tca gtg     1686
Arg Gln Met Leu Pro Val Ile Arg Ser Thr Ala Gly Gly Asp Ser Val
535                 540                 545 cag atc tgc aca aac ccg ctg gac acc ttc ttc ccc ttt gat ccc tgt     1734
Gln Ile Cys Thr Asn Pro Leu Asp Thr Phe Phe Pro Phe Asp Pro Cys
550                 555                 560                 565 gtg ctg aag agg tca aag aaa ttc att gat cct att tat cag gtg tgg     1782
Val Leu Lys Arg Ser Lys Lys Phe Ile Asp Pro Ile Tyr Gln Val Trp
                570                 575                 580 gaa gac atg agt gct gaa gag cta cag gag ttc aag aaa ccc atg aaa     1830
Glu Asp Met Ser Ala Glu Glu Leu Gln Glu Phe Lys Lys Pro Met Lys
            585                 590                 595 aag gac ata gtg gaa gat gaa gat gat gac ttt ctg aaa ggc gaa gtg     1878
Lys Asp Ile Val Glu Asp Glu Asp Asp Asp Phe Leu Lys Gly Glu Val
            600                 605                 610 ccc cag aat gat acc gtg att ggg atc aca cca agc tcc ttt gac acg     1926
Pro Gln Asn Asp Thr Val Ile Gly Ile Thr Pro Ser Ser Phe Asp Thr
    615                 620                 625 cat ttc cga agt cct tca agt agt gtg ggc tcc cca ccc gtg ttg tac     1974
His Phe Arg Ser Pro Ser Ser Ser Val Gly Ser Pro Pro Val Leu Tyr
630                 635                 640                 645 atg caa ccc agt ccc ctc tgacggcaga aatttgtgac tgagatgtga           2022
Met Gln Pro Ser Pro Leu
                650 catttgggat tccccatc                                                 2040
```

```
<210> SEQ ID NO 2
<211> LENGTH: 651
<212> TYPE: PRT
<213> ORGANISM: Homo sapiens
<220> FEATURE:
<221> NAME/KEY: misc_feature
<222> LOCATION: (228)..(228)
<223> OTHER INFORMATION: The 'Xaa' at location 228 stands for Asn, Asp,
      His, or Tyr.
<221> NAME/KEY: misc_feature
<222> LOCATION: (466)..(466)
```

<223> OTHER INFORMATION: The 'Xaa' at location 466 stands for Thr, Ala, Pro, or Ser.

<400> SEQUENCE: 2

```
Met Ala Ala Pro Leu Leu His Thr Arg Leu Pro Gly Asp Ala Ala Ala
1               5                   10                  15

Ser Ser Ser Ala Val Lys Lys Leu Gly Ala Ser Arg Thr Gly Ile Ser
            20                  25                  30

Asn Met Arg Ala Leu Glu Asn Asp Phe Phe Asn Ser Pro Pro Arg Lys
        35                  40                  45

Thr Val Arg Phe Gly Gly Thr Val Thr Glu Val Leu Leu Lys Tyr Lys
    50                  55                  60

Lys Gly Glu Thr Asn Asp Phe Glu Leu Leu Lys Asn Gln Leu Leu Asp
65                  70                  75                  80

Pro Asp Ile Lys Asp Asp Gln Ile Ile Asn Trp Leu Leu Glu Phe Arg
                85                  90                  95

Ser Ser Ile Met Tyr Leu Thr Lys Asp Phe Glu Gln Leu Ile Ser Ile
            100                 105                 110

Ile Leu Arg Leu Pro Trp Leu Asn Arg Ser Gln Thr Val Val Glu Glu
        115                 120                 125

Tyr Leu Ala Phe Leu Gly Asn Leu Val Ser Ala Gln Thr Val Phe Leu
    130                 135                 140

Arg Pro Cys Leu Ser Met Ile Ala Ser His Phe Val Pro Pro Arg Val
145                 150                 155                 160

Ile Ile Lys Glu Gly Asp Val Asp Val Ser Asp Ser Asp Asp Glu Asp
                165                 170                 175

Asp Asn Leu Pro Ala Asn Phe Asp Thr Cys His Arg Ala Leu Gln Ile
            180                 185                 190

Ile Ala Arg Tyr Val Pro Ser Thr Pro Trp Phe Leu Met Pro Ile Leu
        195                 200                 205

Val Glu Lys Phe Pro Phe Val Arg Lys Ser Glu Arg Thr Leu Glu Cys
    210                 215                 220

Tyr Val His Xaa Leu Leu Arg Ile Ser Val Tyr Phe Pro Thr Leu Arg
225                 230                 235                 240

His Glu Ile Leu Glu Leu Ile Ile Glu Lys Leu Leu Lys Leu Asp Val
                245                 250                 255

Asn Ala Ser Arg Gln Gly Ile Glu Asp Ala Glu Glu Thr Ala Thr Gln
            260                 265                 270

Thr Cys Gly Gly Thr Asp Ser Thr Glu Gly Leu Phe Asn Met Asp Glu
        275                 280                 285

Asp Glu Glu Thr Glu His Glu Thr Lys Ala Gly Pro Glu Arg Leu Asp
    290                 295                 300

Gln Met Val His Pro Val Ala Glu Arg Leu Asp Ile Leu Met Ser Leu
305                 310                 315                 320

Val Leu Ser Tyr Met Lys Asp Val Cys Tyr Val Asp Gly Lys Val Asp
                325                 330                 335

Asn Gly Lys Thr Lys Asp Leu Tyr Arg Asp Leu Ile Asn Ile Phe Asp
            340                 345                 350

Lys Leu Leu Leu Pro Thr His Ala Ser Cys His Val Gln Phe Phe Met
        355                 360                 365

Phe Tyr Leu Cys Ser Phe Lys Leu Gly Phe Ala Glu Ala Phe Leu Glu
    370                 375                 380

His Leu Trp Lys Lys Leu Gln Asp Pro Ser Asn Pro Ala Ile Ile Arg
385                 390                 395                 400
```

-continued

```
Gln Ala Ala Gly Asn Tyr Ile Gly Ser Phe Leu Ala Arg Ala Lys Phe
                405                 410                 415
Ile Pro Leu Ile Thr Val Lys Ser Cys Leu Asp Leu Val Asn Trp
        420                 425                 430
Leu His Ile Tyr Leu Asn Asn Gln Asp Ser Gly Thr Lys Ala Phe Cys
            435                 440                 445
Asp Val Ala Leu His Gly Pro Phe Tyr Ser Ala Cys Gln Ala Val Phe
    450                 455                 460
Tyr Xaa Phe Val Phe Arg His Lys Gln Leu Leu Ser Gly Asn Leu Lys
465                 470                 475                 480
Glu Gly Leu Gln Tyr Leu Gln Ser Leu Asn Phe Glu Arg Ile Val Met
                485                 490                 495
Ser Gln Leu Asn Pro Leu Lys Ile Cys Leu Pro Ser Val Val Asn Phe
            500                 505                 510
Phe Ala Ala Ile Thr Asn Lys Tyr Gln Leu Val Phe Cys Tyr Thr Ile
        515                 520                 525
Ile Glu Arg Asn Asn Arg Gln Met Leu Pro Val Ile Arg Ser Thr Ala
    530                 535                 540
Gly Gly Asp Ser Val Gln Ile Cys Thr Asn Pro Leu Asp Thr Phe Phe
545                 550                 555                 560
Pro Phe Asp Pro Cys Val Leu Lys Arg Ser Lys Lys Phe Ile Asp Pro
                565                 570                 575
Ile Tyr Gln Val Trp Glu Asp Met Ser Ala Glu Glu Leu Gln Glu Phe
            580                 585                 590
Lys Lys Pro Met Lys Lys Asp Ile Val Glu Asp Glu Asp Asp Phe
        595                 600                 605
Leu Lys Gly Glu Val Pro Gln Asn Asp Thr Val Ile Gly Ile Thr Pro
    610                 615                 620
Ser Ser Phe Asp Thr His Phe Arg Ser Pro Ser Ser Val Gly Ser
625                 630                 635                 640
Pro Pro Val Leu Tyr Met Gln Pro Ser Pro Leu
                645                 650

<210> SEQ ID NO 3
<211> LENGTH: 627
<212> TYPE: PRT
<213> ORGANISM: Saccharomyces cerevisiae

<400> SEQUENCE: 3

Met Met Ala Phe Glu Asn Thr Ser Lys Arg Pro Pro Gln Asp Phe Val
1               5                   10                  15
Ala Pro Ile Asp Gln Lys Lys Arg Lys Val Gln Phe Ser Asp Ser Thr
            20                  25                  30
Gly Leu Val Thr Leu Gln Pro Glu Glu Ile Lys Asp Glu Val Phe Ser
        35                  40                  45
Ala Ala Met Tyr Ser Arg Phe Val Lys Ser Ala Leu Asp Asp Leu Asp
    50                  55                  60
Lys Asn Asp Ser Thr Gln Ile Gly Ile Ile Ala Asn Gln Val Ala Leu
65                  70                  75                  80
Pro Ser Lys Asn Pro Glu Arg Ile Asn Asp Lys Asn Leu Asn Ile Leu
                85                  90                  95
Leu Asp Ile Leu Ser Ser Asn Ile Asn Arg Ile Glu Ser Ser Arg Gly
            100                 105                 110
Thr Phe Leu Ile Gln Ser Ile Ile Asn Phe Glu Lys Trp Trp Glu Leu
```

```
              115                 120                 125
Pro Pro His Thr Leu Ser Lys Tyr Ile Tyr Phe Ile Lys Ile Leu Cys
    130                 135                 140

Ser Ser Ile Pro Lys Trp Trp Gln Asp Val Ser Met Ile Leu Val Ser
145                 150                 155                 160

Cys Phe Ile Leu Pro Ile Lys Gln Thr Val Cys His His Asp Met Leu
                165                 170                 175

Lys Tyr Phe Leu Arg Met Ile Pro Ser Ser Met Gly Phe Ile Asp Thr
            180                 185                 190

Tyr Leu Ala Lys Phe Phe Pro Asn Lys Asn Asp Thr Arg Arg Lys Leu
        195                 200                 205

Val Asn Tyr Thr Ser Asn Leu Leu Lys Leu Arg Gly Tyr Cys Ser Glu
    210                 215                 220

Leu Gly Phe Gln Ile Trp Ser Leu Leu Ile Glu Lys Ile Ile Ser Ile
225                 230                 235                 240

Asp Val Glu Leu Gln Asn Glu Leu Asp Glu Leu Asp Asp Val Asp
                245                 250                 255

Asp Asp Asp Leu Glu Glu Val Asp Leu Glu Asp Asp Asp Leu Asp
                260                 265                 270

Asp Asp Ser Gly Asp Asp Asp Glu Asn Cys Gly Asn Ser Asn Glu
            275                 280                 285

Glu Leu Arg Ser Gly Ala Ala Asp Gly Ser Gln Ser Asp Ser Glu Asp
        290                 295                 300

Met Asp Ile Ile Glu Gly Met Asp Gly Thr Glu Glu Tyr Asn Val Glu
305                 310                 315                 320

Leu Thr Gln Gly Ile Lys Glu Leu Ser Thr Lys Leu Asp Ser Ile Leu
                325                 330                 335

Thr Leu Val Ser Thr His Val Glu Glu Gln Val Thr Pro Glu Ser Leu
                340                 345                 350

Glu Ser Gly Glu Gly Val Gly Val Phe Asn Thr Leu Thr Thr Leu Phe
            355                 360                 365

Lys Thr His Val Leu Pro Thr Tyr Tyr Thr Arg Ser Ile Gln Tyr Ile
        370                 375                 380

Met Phe His Val Ser Gln Gln Leu Glu Leu Met Asp Ser Phe Leu
385                 390                 395                 400

Val Thr Leu Ile Asp Ile Ser Phe Ala Val Asn Glu Ala Ala Glu Lys
                405                 410                 415

Lys Ile Lys Ser Leu Gln Tyr Leu Gly Ser Tyr Ile Ala Arg Ala Lys
            420                 425                 430

Lys Leu Ser Arg Thr Gln Ile Ile Phe Val Ala Ser Tyr Leu Thr Ser
        435                 440                 445

Trp Leu Asn Arg Tyr Val Ile Glu Arg Glu Glu Val Asp Gln Arg
    450                 455                 460

Gly Gly Met Glu Arg Phe Lys His Phe Tyr Ala Ala Phe Gln Ala Leu
465                 470                 475                 480

Cys Tyr Ile Phe Cys Phe Arg His Asn Ile Phe Arg Asp Thr Asp Gly
                485                 490                 495

Asn Trp Glu Cys Glu Leu Asp Lys Phe Phe Gln Arg Met Val Ile Ser
            500                 505                 510

Lys Phe Asn Pro Leu Lys Phe Cys Asn Glu Asn Val Met Leu Met Phe
        515                 520                 525

Ala Arg Ile Ala Gln Gln Glu Ser Val Ala Tyr Cys Phe Ser Ile Ile
    530                 535                 540
```

-continued

```
Glu Asn Asn Asn Glu Arg Leu Arg Gly Ile Ile Gly Lys Ala Asp
545                 550                 555                 560

Ser Asp Lys Lys Glu Asn Ser Ala Gln Ala Asn Thr Thr Ser Ser Ser
                565                 570                 575

Trp Ser Leu Ala Thr Arg Gln Gln Phe Ile Asp Leu Gln Ser Tyr Phe
                580                 585                 590

Pro Tyr Asp Pro Leu Phe Leu Lys Asn Tyr Lys Ile Leu Met Lys Glu
            595                 600                 605

Tyr Tyr Ile Glu Trp Ser Glu Ala Ser Gly Glu Tyr Glu Ser Asp Gly
        610                 615                 620

Ser Asp Asp
625

<210> SEQ ID NO 4
<211> LENGTH: 599
<212> TYPE: PRT
<213> ORGANISM: Schizosaccharomyces pombe

<400> SEQUENCE: 4

Met Pro Ser Ile Ile Ser Ser Thr Asn Pro Gln Tyr Ile Asn Lys Cys
1               5                   10                  15

Val Asn Asn Gly Thr Met Ala Ser Ser Thr Asn Val Pro Asp Arg Thr
            20                  25                  30

Val Gly Ser Lys Ser Phe Ala Ser Ser Val Ser Lys Asn Asp Gly Arg
        35                  40                  45

Leu Met Gln Gln Met Leu Arg Ala Phe Val Asn Lys Ala Leu Asp Asp
    50                  55                  60

Lys Ala Glu Gly Asn Phe Ala Gly Tyr Glu Asp Leu Arg Arg Gln Phe
65                  70                  75                  80

Ala Ala Lys Ser Asp Thr Lys Asp Ala Pro Ser Ser Leu Gln Leu Gln
                85                  90                  95

Asn Leu Leu Ser Ala Leu Thr Cys Asn Val Ser Arg Leu Asp Ser Ser
            100                 105                 110

Asn Ser Ser Leu Val Met Ser Val Leu Asp Ser Val Trp Val Ser Arg
        115                 120                 125

Asp Glu Ser Phe Val Arg Cys Tyr Thr Arg Phe Leu Gly Asn Leu Ile
    130                 135                 140

Ser Ala Gln Ser Asn Tyr Leu Pro Leu Val Met Thr Met Leu Ile Gln
145                 150                 155                 160

His Met Leu Tyr Arg Pro Asp Ser Leu Ala Ile His Tyr Glu His Ala
                165                 170                 175

His Met Ala Leu Lys Tyr Val Leu Glu Leu Val Pro Arg Ala His Ser
            180                 185                 190

Phe Leu Tyr Ser Ser Ile Leu Glu Glu Phe Pro Tyr Lys Asp Glu Ser
        195                 200                 205

Leu Leu Ala Gln Met Thr Tyr Ile Ser Asn Val Leu Ser Ile Cys Glu
    210                 215                 220

Tyr Val Pro Ser Ile Lys Gly Pro Val Leu His Ala Ile Ile Asp Lys
225                 230                 235                 240

Ile Ile Gln Ile Asp Val Glu Ile Gln Val Glu Val Asp Asp Asp
                245                 250                 255

Glu Glu Glu Asp Glu Val Val Thr Asp Asp Gly Thr Ser Asn Ala
            260                 265                 270

Asp Ser Glu Val Ile Thr Ala Ser Thr Leu Tyr Glu Arg His Thr Ala
```

-continued

```
                275                 280                 285
Ile Ser Ser Glu Met Thr Ser Ser Thr Ile Leu Thr Pro Pro Ser Leu
        290                 295                 300

Thr Asp Thr Arg Gln Leu Met Gln Gln Leu Asp Gln Leu Leu Tyr Thr
305                 310                 315                 320

Leu Phe Ser Tyr Leu Asp Ser Asn Leu Lys Ser Thr Ser Arg Asp Arg
                325                 330                 335

Tyr Leu Val Tyr Asn Ser Leu Ile Lys Ser Phe Val Asn Thr Val Leu
                340                 345                 350

Lys Thr Phe Arg Cys Arg Tyr Thr Gln Phe Leu Ile Phe Trp Ala Ser
                355                 360                 365

Gln Leu Asp Pro Glu Phe Thr Asp Ile Phe Leu Gly Val Leu Thr Glu
        370                 375                 380

Val Cys Leu Asp Pro Ser Gln Pro Tyr Thr Leu Arg Leu Ser Gly Ala
385                 390                 395                 400

Met Tyr Ile Gly Ser Tyr Val Ala Arg Ala Lys Ala Leu Glu Lys Asn
                405                 410                 415

Thr Ile Gln Ile Ile Val Asn Met Met Thr Arg Trp Val Glu Ala Tyr
                420                 425                 430

Leu Asp Gln Cys Glu Asn Glu Leu Ser Asp Asp Leu Leu Ser Lys His
                435                 440                 445

Ser Val Phe Tyr Ala Ile Asn Gln Ser Ile Phe Tyr Ile Phe Cys Phe
        450                 455                 460

Arg Trp Arg Glu Leu Cys Val Ser Asp Glu Ser Glu Ser Met Glu Pro
465                 470                 475                 480

Arg Pro Asn Glu Trp Ile Pro Gly Leu Glu Ile Leu His Arg Ser Val
                485                 490                 495

Leu Ser Arg Leu Asn Pro Leu Arg Tyr Cys Ser Pro Asn Ile Val Leu
                500                 505                 510

Gln Phe Ala Lys Val Ala Asn His Leu Asn Phe Met Tyr Val Tyr Ser
                515                 520                 525

Ile Ile Glu Gln Asn Arg Lys Gly Ile Phe Arg Glu Gly Phe Asp Thr
        530                 535                 540

Met Asp Ala Tyr Phe Pro Phe Asp Pro Tyr Arg Leu Thr Lys Ser Ser
545                 550                 555                 560

Ile Ile Val Gln Pro Phe Tyr Asn Glu Trp Gln Gln Ile Pro Gly Leu
                565                 570                 575

Asp Asp Asp Glu Glu Glu Asp Thr Asp Tyr Glu Ser Ser Thr Val
                580                 585                 590

Met Leu Gly Glu Ser Pro Phe
        595
```

<210> SEQ ID NO 5
<211> LENGTH: 654
<212> TYPE: PRT
<213> ORGANISM: Caenorhabditis elegans

<400> SEQUENCE: 5

```
Met Lys Arg Ser Thr Ala Asn Ala Pro Lys Leu Ser Pro Lys His Glu
1               5                   10                  15

Ser Glu Ser Asp Pro Lys Lys Val Lys Leu Glu Glu Ala Lys Pro
                20                  25                  30

Thr Val Asn Gln Ala Pro Thr Gly Arg Glu Ile Val Glu Asn Tyr Leu
        35                  40                  45
```

```
Lys Gly Asp Val Thr Ala Ala Val Leu Tyr Arg Lys Ile Cys Asn Ala
 50                  55                  60

Leu Glu Thr Phe Glu Gln Trp Glu Ser Glu Ala Pro Lys Ile Gln Leu
 65                  70                  75                  80

Leu Asp Gln Phe Leu Asn Ile Ala Asp Ala Met Glu Ala Arg Thr Glu
                 85                  90                  95

Thr Leu Val Lys Arg Leu Leu Ser Leu Arg Trp Asp Lys Ile Pro Gly
            100                 105                 110

Ser Val Ile Glu Arg Phe Arg Asn Phe Leu Cys Glu Leu Ala Ile Arg
            115                 120                 125

His Leu Cys Phe Thr Glu Val Tyr Ser Ala Val Val Glu Arg Leu
130                 135                 140

Val Pro Gln Ile Ser Val Thr Glu Glu Thr Gly Val Val Thr Leu Ile
145                 150                 155                 160

Leu Thr Glu Lys Val Gln Asn Glu His Phe Glu Met Ala His Ile
                165                 170                 175

Ile Ser Ser Val Leu Arg Cys Phe Pro Leu Ser Ala Arg Ala Leu Leu
                180                 185                 190

Lys Cys Val Lys Arg Val Met Pro His Phe Thr Arg Pro Ser Val Thr
            195                 200                 205

Val Ala Gly Tyr Met Arg Asn Leu Ile Leu Met Gln Lys Tyr Ile Pro
210                 215                 220

Ala Ser Ile Ser Lys Asp Val Trp Glu Ala Val Phe Glu Arg Leu Ala
225                 230                 235                 240

Lys Asp Asp Thr His Asn Trp Lys Cys Glu Gln Asn Glu Glu Met Ser
                245                 250                 255

Lys Ser Pro Arg Leu Phe Ala Leu Asn Asp Asp Ile Leu Ile Glu Glu
            260                 265                 270

Val Val Glu Gly Asn Thr Asn Asp Ser Glu Asp Val Thr Pro Glu Gln
            275                 280                 285

Leu Glu Gln Arg Lys Gly Glu Gln Met Ile Gln Tyr Leu Asp Ser Val
290                 295                 300

Cys Thr Asp Val Ile Thr Phe Ile Arg Ser Ser Val Asp Ser Glu Ile
305                 310                 315                 320

Asp Glu Glu Asn Gly Asn Glu Arg Thr Lys Leu Asn Asp Lys Trp Leu
                325                 330                 335

Arg Asn Phe Lys Ile Thr Gly Asp Lys Val Leu Pro Lys Glu Lys Leu
            340                 345                 350

Phe Asp Thr Phe Leu Glu Cys Leu Glu Ser Thr Met Leu Asn Ala Thr
        355                 360                 365

His Val Gln Tyr Val Ser Phe Ile Trp Leu Tyr Phe Cys Ser Leu Ser
    370                 375                 380

Gln Glu Tyr Glu Lys Lys Met Leu Glu His Leu Trp Gln Val Thr Ile
385                 390                 395                 400

Arg Met Pro Arg Ala Pro Ala Asp Ala Arg Lys Ser Gln Gly Ala Ala
                405                 410                 415

Ser Tyr Leu Ala Ala Phe Leu Ala Arg Ala Lys Tyr Val Lys Lys Ser
            420                 425                 430

Thr Ala Phe Thr Trp Leu Glu Glu Val Tyr Ile Trp Leu Arg His Tyr
        435                 440                 445

Val Asp Gln Phe Gly Ser Gly Ser Ser Gln Ile Leu Pro Gly Leu Gln
    450                 455                 460

Arg His Gly Thr Phe Tyr Ser Val Ser Gln Ala Phe Phe Leu Val Phe
```

```
                    465                 470                 475                 480

Ala Phe Arg Tyr Lys Glu Phe Val Lys Asn Lys Asp Met Leu Glu Thr
                        485                 490                 495

Ile Arg Arg Trp Gly Val Gly Arg Val Val His Ser Pro Leu Glu Pro
                        500                 505                 510

Leu Lys Tyr Val Ser Lys Pro Val Ala Arg Cys Phe Ser Ala Ile Thr
                        515                 520                 525

Arg Ser Leu Gln Leu Val Tyr Cys Asn His Ile Ile Pro Ile Glu Glu
                        530                 535                 540

Val Gln Arg Pro Phe Asp Asp Met Phe Pro Phe Asp Cys Tyr His Leu
        545                 550                 555                 560

Lys Glu Ser Ser Lys Phe Met Thr Pro Leu Met Arg Lys Phe Ser Pro
                        565                 570                 575

Leu Ala Glu Asp Met Ser Thr Leu Thr Lys Ala Leu Cys Trp Asn Ala
                        580                 585                 590

Ala Thr Ala Asp Lys Ser Glu Lys Ser Ala Glu Ala Val Ser Ser Ser
                        595                 600                 605

Glu Gly Leu Asp Phe Leu Asp Glu Asp Ala Met Met Met Gly Gly
                        610                 615                 620

Ser Ser Gly Tyr Arg Glu Arg Thr Phe Ser Cys Gly Gln Ser Ser Leu
        625                 630                 635                 640

Ile Asn Tyr Ser Ala Thr Pro Gly Leu Gln Thr Phe Asn Val
                        645                 650

<210> SEQ ID NO 6
<211> LENGTH: 602
<212> TYPE: PRT
<213> ORGANISM: Arabidopsis thaliana

<400> SEQUENCE: 6

Met Gly Ala Val Glu Leu Met Ser Asp Pro Ser Ser Leu Cys Thr Val
        1               5                   10                  15

Glu Asn Tyr Val Asp Asn Val Asp Leu Ser Asp Thr Gln Leu Val Gln
                        20                  25                  30

Thr Val Arg Lys Ala Leu Thr Ser Val Lys Thr Gly Asp Ser Asp Leu
                        35                  40                  45

Tyr Ser Glu Met Val Gly Val Met Ala Arg Asp Ile Lys Glu Phe Lys
                        50                  55                  60

Asp Pro Asp Val Val Ala Gln Leu Glu Thr Val Leu Lys Ala Leu Ser
        65                  70                  75                  80

Gly Ala Val Ala Cys Ile Asp Val Leu His His Gln Lys Leu Leu Ser
                        85                  90                  95

Ala Leu Phe Arg Met Lys Leu Trp Asp His Arg Pro Asp Val Met Asp
                        100                 105                 110

Ala Leu Val Asn Leu Val Ile Ser Leu Ala Val Thr Ser Gly Lys Tyr
                        115                 120                 125

Leu Asp Ser Cys Leu Asn Met Leu Val Ser Asn Phe Val Pro Pro Pro
                        130                 135                 140

Trp Val Asn Asn Leu Ser His Ser Arg Ile Leu Asn Lys Lys Ile
        145                 150                 155                 160

Asp Val Leu Ser Arg Val His Ala Ala Leu Leu Lys Ile Ser Ile Leu
                        165                 170                 175

Val Pro Leu Thr Pro Ser Arg Leu Val Pro Met Leu Phe Gln Gln Met
                        180                 185                 190
```

```
Pro Lys Met His Lys Lys Asp His Ser Ile Val Ile Tyr Val Glu Ser
    195                 200                 205

Leu Leu Lys Leu Glu Asn Ser Ser Ile Gly Gln Val Gly Ser Met
210                 215                 220

Ile Leu Gly Met Val Met Glu Arg Leu Arg Asp Leu Asp Val Ser Arg
225                 230                 235                 240

Gln Asn Met Leu Ile Gln Leu Arg Ser Leu Glu Ile Glu Trp Asp Asp
                245                 250                 255

Ile Pro Gln Asp Asp Ser Ser Arg Gly Met Phe Asp Met Glu Leu Glu
                260                 265                 270

Asp Ala Ala Glu Gly Thr Met Asn Asp Gly Asp Cys Leu Pro Val Gly
            275                 280                 285

Pro Leu Lys Gln Asp Thr Ser Asp Gly Ser Ile Val Ser Lys Leu Leu
            290                 295                 300

Asp Lys Leu Met Val Val Ala Phe Glu His Leu Glu Ser Cys Gln Asn
305                 310                 315                 320

Asp Gly Arg Leu Asp Gln Val Phe Glu Ser Leu Phe Lys Ser Phe Glu
                325                 330                 335

Asn Phe Ile Leu Asn Thr Tyr Lys Ser Lys Phe Thr Gln Phe Leu Ile
                340                 345                 350

Phe Tyr Ala Cys Ser Leu Asp Pro Glu Asn Cys Gly Val Lys Phe Ala
            355                 360                 365

Ser Lys Leu Val Glu Ile Phe Leu Ser Ser Asn Lys His Val Ala Thr
    370                 375                 380

Arg Gln Ala Ser Leu Arg Leu Ile Asp Glu Cys Val Gly Tyr Cys Arg
385                 390                 395                 400

Thr Cys Asn Asp Asp Thr Arg Pro Glu Ala His Gln Ile Phe Phe Ser
                405                 410                 415

Gly Cys Gln Ala Ile Met Tyr Val Leu Cys Phe Arg Met Arg Ser Ile
            420                 425                 430

Leu Asp Val Pro Arg Phe Arg Ser Gln Leu Thr Pro Leu Glu Ser Ile
            435                 440                 445

Leu Met His Lys Leu Asn Pro Leu Met Val Cys Leu Pro Ser Val Val
    450                 455                 460

Ala Glu Phe Leu Arg Gln Ala Lys Glu Gly Gly Leu Phe Ile Val Ser
465                 470                 475                 480

Asp Ser Phe Ile Phe Asp Asp Leu Leu Glu Ser Glu Leu Ser Arg Ala
                485                 490                 495

Phe Gly Gly Phe Glu Arg Leu Asp Thr Phe Phe Pro Phe Asp Pro Cys
            500                 505                 510

Leu Leu Lys Ser Ser Asn Ser Phe Ile Ser Pro Asn Phe Ile Tyr Trp
            515                 520                 525

Ser Met Val Lys Ala Thr Tyr Asp Glu Asp Asp Asp Asn Asp Ala
    530                 535                 540

Glu Val Ile Val Asn Gly Asp Glu Asp Ser Asp Glu Asp Asp Glu Ala
545                 550                 555                 560

Asp Leu Asp Tyr Ala Leu Asn Lys Met Ser Ile Thr Pro Lys His Ser
                565                 570                 575

Phe Lys Asn Lys Met Glu Arg Asp Arg Leu Leu Arg Met Pro Ser Arg
            580                 585                 590

Ile Arg Pro Ser Thr Ser Pro Glu Ser Leu
            595                 600
```

```
<210> SEQ ID NO 7
<211> LENGTH: 191
<212> TYPE: PRT
<213> ORGANISM: Artificial Sequence
<220> FEATURE:
<223> OTHER INFORMATION: Consensus sequence for the C-terminal region
<221> NAME/KEY: MISC_FEATURE
<222> LOCATION: (38)..(38)
<223> OTHER INFORMATION: Xaa is any amino acid
<221> NAME/KEY: MISC_FEATURE
<222> LOCATION: (54)..(54)
<223> OTHER INFORMATION: Xaa is any amino acid
<221> NAME/KEY: MISC_FEATURE
<222> LOCATION: (81)..(106)
<223> OTHER INFORMATION: Xaa is any amino acid
<221> NAME/KEY: MISC_FEATURE
<222> LOCATION: (143)..(145)
<223> OTHER INFORMATION: Xaa is any amino acid

<400> SEQUENCE: 7

Phe Asn Ser Leu Phe Lys Ser Phe Glu Asn Thr Val Leu Asn Thr Tyr
 1               5                  10                  15

Lys Ser Arg Tyr Thr Gln Phe Leu Ile Phe Tyr Ala Cys Ser Leu Asp
            20                  25                  30

Pro Glu Asn Cys Asp Xaa Phe Leu Ser Lys Leu Val Glu Val Phe Leu
        35                  40                  45

Ser Ser Asn Lys Ala Xaa Ala Lys Arg Gln Ala Ser Ala Arg Tyr Ile
 50                  55                  60

Gly Ser Tyr Val Ala Arg Ala Lys Thr Leu Asn Lys Asp Thr Ile Pro
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Glu Arg His Gln Ile Phe
            100                 105                 110

Tyr Ser Gly Cys Gln Ala Ile Phe Tyr Val Phe Cys Phe Arg Met Arg
            115                 120                 125

Glu Phe Leu Asp Val Asp Arg Phe Arg Ser Gln Glu Thr Arg Xaa Xaa
        130                 135                 140

Xaa Glu Arg Ile Val Met Ser Lys Leu Asn Pro Leu Lys Tyr Cys Ser
145                 150                 155                 160

Pro Asn Val Val Leu Glu Phe Ala Arg Ile Ala Lys Glu Leu Gly Leu
                165                 170                 175

Phe Tyr Val Ser Ser Ile Ile Glu Phe Asn Asp Leu Leu Arg Ser
                180                 185                 190
```